United States Patent [19]
Utz et al.

[11] Patent Number: 6,143,830
[45] Date of Patent: Nov. 7, 2000

[54] EMULSIFIER COMPOSITION COMPRISING ETHYLENE OXIDE/PROPYLENE OXIDE BLOCK COPOLYMERS AND AMINE-CONTAINING ETHYLENE OXIDE/PROPYLENE OXIDE BLOCK COPOLYMERS

[75] Inventors: Christopher G. Utz; Johnny M. Sekmistrz, both of Wyandotte, Mich.

[73] Assignee: BASF Corporation, Mt. Olive, N.J.

[21] Appl. No.: 09/135,494

[22] Filed: Aug. 17, 1998

[51] Int. Cl.[7] .......................... C08L 23/04; C08L 25/02; A01N 55/00; A01N 57/00
[52] U.S. Cl. .......................... 525/240; 525/241; 514/80; 514/63; 514/941; 424/83
[58] Field of Search .................. 514/941, 80, 63; 424/83; 455/106; 560/240; 525/240, 241

[56] References Cited

U.S. PATENT DOCUMENTS

| | | | |
|---|---|---|---|
| 4,276,054 | 6/1981 | Schmolka et al. | 44/51 |
| 4,313,847 | 2/1982 | Chasin et al. | 252/356 |
| 4,452,712 | 6/1984 | Laemmle | 252/49.3 |
| 4,585,647 | 4/1986 | Schmolka | 424/45 |
| 4,810,279 | 3/1989 | Martin | 71/121 |
| 4,851,217 | 7/1989 | Mentke | 424/83 |
| 4,904,359 | 2/1990 | Pancheri et al. | 252/548 |
| 4,978,686 | 12/1990 | Sotome | 514/698 |
| 5,354,739 | 10/1994 | Rochling | 514/63 |
| 5,565,188 | 10/1996 | Wong et al. | 424/9.411 |
| 5,622,691 | 4/1997 | Tricaudq | 424/62 |
| 5,674,514 | 10/1997 | Hasslin | 424/405 |
| 5,705,194 | 1/1998 | Wong et al. | 424/489 |
| 5,843,734 | 12/1998 | Shonaka | 435/106 |
| 5,874,498 | 2/1999 | Daniels et al. | 524/563 |
| 5,948,546 | 9/1999 | Bafford et al. | 428/500 |

OTHER PUBLICATIONS

Seymour et al. POlymer Chemistry, second edition, Marcel Dekker, Inc., pp. 73,363,345, 1987.

*Primary Examiner*—David W. Wu
*Assistant Examiner*—Tanya Zalukaeva
*Attorney, Agent, or Firm*—Mark A. Frentrup; Joanne P. Will

[57] ABSTRACT

There is provided an emulsifier composition comprising (a) a blend consisting essentially of a polyoxyethylene (EO)/polyoxypropylene (PO) block copolymer which contains 10–40% EO, and where the molecular weight of the PO hydrophobe is about 500–6000; anionic surfactants; and a solvent; (b) a blend consisting essentially of a polyoxyethylene (EO)/polyoxypropylene (PO) block copolymer which contains 50–80% EO, and where the molecular weight of the PO hydrophobe is about 500–6000; anionic surfactants; and a solvent; and (c) a butyl ether of an EO/PO block copolymer.

11 Claims, No Drawings

EMULSIFIER COMPOSITION COMPRISING ETHYLENE OXIDE/PROPYLENE OXIDE BLOCK COPOLYMERS AND AMINE-CONTAINING ETHYLENE OXIDE/PROPYLENE OXIDE BLOCK COPOLYMERS

FIELD OF THE INVENTION

The present invention relates to emulsifier compositions comprising ethylene oxide/propylene oxide (EO/PO) block copolymers, anionic surfactants and various solvents and butyl ethers.

BACKGROUND OF THE INVENTION

Aqueous emulsions useful for formulating pesticidal compositions are known to those skilled in the art. Specifically, U.S. Pat. No. 4,283,222 discloses an emulsifiable concentrate for weed control containing an emulsifier and a hydrocarbon and ketonic solvent. The emulsifiers are at least one anionic surfactant and at least two nonionic surfactants. The anionic surfactants are selected from calcium salts of alkylbenzenesulfonates. The nonionic surfactants are selected from polyoxyalkylene alkyl ethers and polyoxyethylene/polyoxypropylene polymers. The hydrocarbon solvents are, for example, benzene, toluene. The ketonic solvents are, for example, methylamylketone and ethyl-n-butylketone. U.S. Pat. No. 4,351,753 discloses emulsifiers for pesticidal concentrates. Said emulsifiers comprise nonionic polyoxyalkylene block copolymers, ethylene glycol, and water. The nonionic polyoxyalkylene block copolymers can be amine-containing or not. No anionic surfactants are disclosed. U.S. Pat. No. 4,382,013, U.S. Pat. No. 4,450,001 and U.S. Pat. No. 4,464,193 disclose emulsifiers for biocides. Said emulsifiers comprise anionic glycol ester surfactants, alkyl aromatic sulfate anionic surfactants and nonionic polyoxyalkylene surfactants (amine-containing or non-amine-containing). U.S. Pat. No. 4,810,279 discloses herbicidal oil in water compositions comprising herbicide, alkyl phenol polyethylene oxide condensates, EO/PO block copolymers and anionic surfactants. U.S. Pat. No. 4,904,683 discloses nonionic emulsifiers for pesticides containing polyoxyalkylene/polyoxypropylene block copolymers and anionic surfactants (e.g. dodecylbenzenesulfonic acid). U.S. Pat No. 4,929,608 discloses emulsifier compositions for pesticides containing ethoxylated nonionic surfactants and anionic surfactants. Said nonionic surfactants are selected from a blend of ethoxylated nonionic surfactants, e.g. (FLO MO® products) or nonylphenol. Said anionic surfactants are calcium alkylaryl sulfonates. U.S. Pat. No. 5,354,739 discloses emulsifiers for pesticides containing anionic and nonionic surfactants and short-chain or long-chain alcohols. Said anionic surfactants include salts of dodecylbenzenesulfonic acids. The nonionic surfactants include castor oil oxyethylates, polyoxyethylene/polyoxypropylene copolymers, and ethoxylated alkylphenols. The short-chain alcohols are $C_2$–$C_3$ and the long-chain alcohols are $C_4$–$C_{16}$. Finally, U.S. Pat No. 5,674,514 discloses emulsifiers for pesticides containing anionic surfactants, nonionic surfactants (amine- and non-amine-containing) and insoluble polymers such as polystyrenes, polyvinylchloride and polymethylmethacrylate.

However, the art does not disclose the Applicants' invention wherein amine-containing and non-amine-containing polyoxyethylene/polyoxypropylene (EO/PO) block copolymers are blended in a single emulsifier composition.

SUMMARY

An emulsifier composition comprising:
(a) 1–90% of a blend consisting essentially of:
  (i) a polyoxyethylene (EO)/polyoxypropylene (PO) block copolymer selected from Formula I, II or III or mixtures thereof:

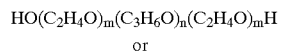

I.

or

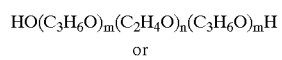

II.

or

III.

wherein Formula I, II and III all contain 10–40% EO, further provided that n has a value such that the molecular weight of the PO hydrophobe is about 1200–4000 for Formula I, 1500–4000 for Formula II and 500–6000 for Formula III;
  (ii) anionic surfactants;
  (iii) a solvent; and
(b) 1–90% of a blend consisting essentially of:
  (i) a polyoxyethylene (EO)/polyoxypropylene (PO) block copolymer selected from Formula I, II or III or mixtures thereof:

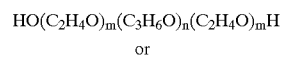

I.

or

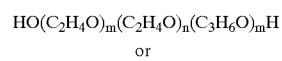

II.

or

III.

wherein Formula I, II and III all contain 50–80% EO, further provided that n has a value such that the molecular weight of the PO hydrophobe is about 1200–4000 for Formula I, 1500–4000 for Formula II and 500–6000 for Formula III;
  (ii) anionic surfactants;
  (iii) a solvent; and
(c) 10–50% butyl ether of an EO/PO block copolymer.

DETAILED DESCRIPTION

An emulsifier composition comprising:
(a) 1–90% of a blend consisting essentially of:
  (i) a polyoxyethylene (EO)/polyoxypropylene (PO) block copolymer (EO/PO block copolymer) selected from Formula I, II or III or mixtures thereof:

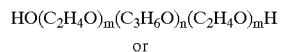

I.

or

-continued $$HO(C_3H_6O)_m(C_2H_4O)_n(C_3H_6O)_mH \quad \text{II.}$$

or

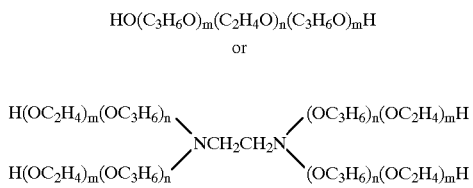   III.

wherein Formula I, II and III all contain 10–40% EO, further provided that n has a value such that the molecular weight of the PO hydrophobe is about 1200–4000 for Formula I, 1500–4000 for Formula II and 500–6000 for Formula III;
(ii) anionic surfactants;
(iii) a solvent; and
(b) 1–90% of a blend consisting essentially of:
 (i) a polyoxyethylene (EO)/polyoxypropylene (PO) block copolymer (EO/PO block copolymer) selected from Formula I, II or III or mixtures thereof:

$$HO(C_2H_4O)_m(C_3H_6O)_n(C_2H_4O)_mH \quad \text{I.}$$

or $$HO(C_3H_6O)_m(C_2H_4O)_n(C_3H_6O)_mH \quad \text{II.}$$

or

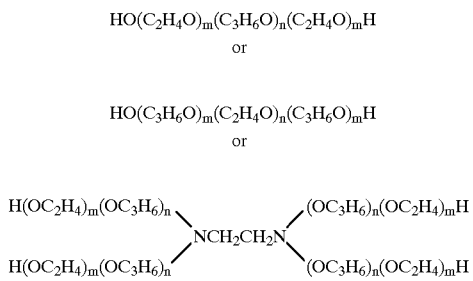   III.

wherein Formula I, II and III all contain 50–80% EO, further provided that n has a value such that the molecular weight of the PO hydrophobe is about 1200–4000 for Formula I, 1500–4000 for Formula II and 500–6000 for Formula III;
(ii) anionic surfactants;
(iii) a solvent; and
c) 10–50% butyl ether of an EO/PO block copolymer.

The emulsifier composition of the present invention is prepared by blending blends (a) and (b) with a butyl ether of an EO/PO block copolymer (Component (c)) according to blending methods known to those skilled in the art, such as those described in U.S. Pat. No. 4,810,279, col 2, lines 56–65, incorporated by reference herein.

The Polyoxyethylene/Polyoxypropylene (EO/PO) Block Copolymer

The EO/PO block copolymer, useful in preparing blends (a) and (b), is selected from Formula I, II or III or mixtures thereof.

   Formula I n is such that the molecular weight of the PO hydrophobe is 1200–4000, preferably 1800–3600, more preferably 2400–3600; most preferably 2700–3000.

Compounds represented by Formula I, and suitable for use in the present invention are available from the BASF Corporation under the trademarks PLURONIC® P104, PLURONIC® F108 and PLURONIC® F98.

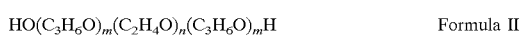   Formula II n is such that the MW of the PO hydrophobe is 1500–4000, preferably 1700–3500, more preferably 2000–3000; most preferably 2500–3100. Compounds represented by Formula II, and suitable for use in the present invention are available from the BASF Corporation as PLURONIC® 17R2 and 25R4.

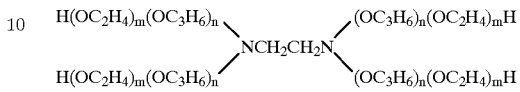   Formula III n is such that the MW of the PO hydrophobe is 500–6000, preferably 1000–5500, more preferably 2000–5000; most preferably 3000–4000. Compounds represented by Formula III, and suitable for use in the present invention are available from the BASF Corporation as TETRONIC® 704 and TETRONIC® 908.

Blend (a) Comprises Elements (i), (ii) and (iii).

Element (i) is an EO/PO block copolymer selected from Formula I, II, or III or mixtures thereof:

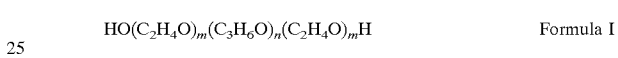   Formula I n is such that the molecular weight of the PO hydrophobe is preferably 1800–3600, more preferably 2400–3600; most preferably 2700–3000.

Compounds represented by Formula I, and suitable for use in the present invention are available from the BASF Corporation under the trademarks PLURONIC® P104, PLURONIC® P123 AND PLURONIC® P84.

or

   Formula II n is such that the MW of the PO hydrophobe is preferably 1700–3500, more preferably 2000–3000; most preferably 2500–3100. Compounds represented by Formula II, and suitable for use in the present invention are available from the BASF Corporation as PLURONIC® 25R4.

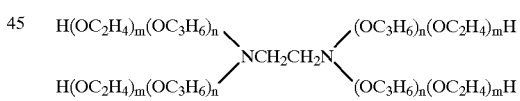   Formula III n is such that the MW of the PO hydrophobe is preferably 1000–5500, more preferably 2000–5000; most preferably 3000–4000. Compounds represented by Formula III, and suitable for use in the present invention are available from the BASF Corporation as TETRONIC® 704 and TETRONIC® 904, or mixtures thereof.

The EO content for Formula I, II and III in Blend (a) is 10–40%.

Preferably element (i) is 1–40% of Blend (a), more preferably 5–25%, and most preferably 10–20% by weight of Blend (a).

Element (ii) is the anionic surfactant. Preferably said anionic surfactant is 20–80% of Blend (a), more preferably 40–70%, and most preferably 55–65% by weight of Blend (a). Element (iii) is the solvent. Preferably said solvent is 10–50% of Blend (a), more preferably 15–40%, and most preferably 20–30% by weight of Blend (a). Solvents useful in the practice of the present invention include $C_4$–$C_{25}$ alcohols such as n-butanol; n-hexanol; n-octanol and tridecyl-alcohol. The most preferred is n-butanol. Hydrocarbon solvents such as AROMATIC® 100 from Exxon Chemical Corp. , ketones such as cyclohexanone, methyl esters such as methyl laurate, and acetate esters such as the EXXATE® (oxo-alcohol acetates) can also be used as element (iii).

In Blend (a), the preferred element (i) is Formula III.

Blend (b) Comprises Elements (i), (ii) and (iii)

Element (i) is an EO/PO block copolymer selected from Formula I, II or III or mixtures thereof:

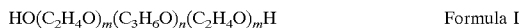
HO(C$_2$H$_4$O)$_m$(C$_3$H$_6$O)$_n$(C$_2$H$_4$O)$_m$H     Formula I n is such that the molecular weight of the PO hydrophobe is preferably 1800–3600, more preferably 2400–3600; most preferably 2700–3000.

Compounds represented by Formula I, and suitable for use in the present invention are available from the BASF Corporation under the trademarks PLURONIC® F108 AND PLURONIC® F98.

or

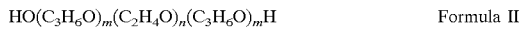
HO(C$_3$H$_6$O)$_m$(C$_2$H$_4$O)$_n$(C$_3$H$_6$O)$_m$H     Formula II n is such that the MW of the PO hydrophobe is preferably 1700–3500, more preferably 2000–3000; most preferably 2500–3100. Compounds represented by Formula II, and suitable for use in the present invention are available from the BASF Corporation as PLURONIC® 25R8.

or

 Formula III

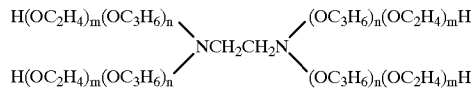

n is such that the MW of the PO hydrophobe is preferably 1000–5500, more preferably 2000–5000; most preferably 3000–4000. Compounds represented by Formula III, and suitable for use in the present invention are available from the BASF Corporation as TETRONIC® 707 and TETRONIC® 908 or mixtures thereof.

The EO content is 50–80% in Formula I, II and III for Blend (b).

Preferably Element (i) is 10–50% of Blend (b), more preferably 20–45%, and most preferably 30–40% by weight of Blend (b).

Element (ii) is the anionic surfactant. Preferably said anionic surfactant is 20–80% of Blend (b), more preferably 35–70%, and most preferably 40–50% by weight of Blend (b). Element (iii) is the solvent. Preferably said solvent alcohol is 10–50% of Blend (b), more preferably 15–40%, and most preferably 20–30% by weight of Blend (b). Solvents useful in the practice of the present invention include $C_4$–$C_{25}$ alcohols such as n-butanol; n-hexanol; n-octanol and tridecyl-alcohol. The most preferred is n-butanol. Hydrocarbon solvents such as AROMATIC® 100 from Exxon Chemical Corp., ketones such as cyclohexanone, methyl esters such as methyl laurate, and acetate esters such as the EXXATE® (oxo-alcohol acetates) can also be used as element (iii).

In Blend (b), the preferred element (i) is Formula III.

Component (c) is 10–50% of a Butyl Ether of an EO/PO Block Copolymer.

The Butyl Ethers of an EO/PO Block Copolymer (Component (c))

Preferred Butyl ethers of EO/PO block copolymers (CAS 9038-95-3) are butyl-omega-hydroxypoly(oxypropylene) block polymer with poly(oxyethylene) having an average molecular weight in a range of 2,400 to 3,500. The most preferred is alpha-butyl-omega-hydroxy-ethylene oxide propylene oxide copolymer having a molecular weight of 3100 and cloud point of 76° C. (e.g. Tergitol® XD, available from Union Carbide Corp.).

Blend (a), blend (b) and Component (c) are blended to achieve the emulsifier composition of the present invention. Blend (a) is preferably 1–90% of the emulsifier composition, more preferably 20–70% and most preferably 25–50% by weight of the emulsifier composition of the present invention.

Blend (b) is preferably 1–90% of the emulsifier composition, more preferably 20–70% and most preferably 25–50% by weight of the emulsifier composition of the present invention.

Component (c) is preferably 10–50% of the emulsifier composition, more preferably 15–40%, and most preferably 20–30% by weight of the emulsifier composition of the present invention.

The Anionic Surfactant

Anionic surfactants (element (ii) in both blends (a) and (b)) useful in the practice of the present invention include, but are not limited to, the water-soluble salts, preferably the alkali metal, ammonium- and substituted-ammonium salts, of organic sulfuric acid reaction products having in their molecular structure an alkyl group containing from about 10 to about 20 carbon atoms and a sulfonic acid or sulfuric acid ester group. (Included in the term "alkyl" is the alkyl portion of acyl groups.) Examples of this group of synthetic surfactants are the sodium and potassium alkyl sulfates, especially those obtained by sulfating the higher alcohols ($C_8$–$C_{18}$ carbon atoms) such as those produced by reducing the glycerides of tallow or coconut oil; and the sodium and potassium alkylbenzenesulfonates in which the alkyl group contains from about 9 to about 15 carbon atoms in straight-chain or branched-chain configuration, e.g., those of the type described in U.S. Pat. Nos. 2,220,099 and 2,477,383 both of which are incorporated herein by reference. Especially valuable are linear straight-chain alkylbenzene sulfonates in which the average number of carbon atoms in the alkyl group is from 11 to 13, abbreviated as $C_{11-13}$LAS (lauryl ammonium sulfate).

Other anionic surfactants suitable for use herein are the sodium alkyl glyceryl ether sulfonates, especially those ethers of higher alcohols derived from tallow and coconut oil; sodium coconut oil fatty acid monoglyceride sulfonates and sulfates; sodium or potassium salts of alkyl phenol ethylene oxide ether sulfates containing from about 1 to about 10 units of ethylene oxide per molecule and from about 8 to about 12 carbon atoms in the alkyl group; and sodium or potassium salts of alkyl ethylene oxide ether sulfates containing from about 1 to about 25 units of ethylene oxide per molecule and from about 10 to about 20 carbon atoms in the alkyl group.

Other useful anionic surfactants include the water-soluble salts of esters of alpha-sulfonated fatty acids containing from about 6 to 20 carbon atoms in the fatty acid group and from about 1 to 10 carbon atoms in the ester group; water-soluble salts of 2-acyloxy-alkane-1-sulfonic acids containing from about 9 to about 23 carbon atoms in the alkyl group and from about 8 to 20 carbon atoms in the moiety.

Preferred surfactants herein are anionic surfactants selected from the group consisting of the alkali metal salts of $C_{11-13}$ alkylbenzene sulfonates, $C_{12-18}$ alkyl sulfates, $C_{12-18}$ alkyl linear polyethoxy sulfates containing from about 1 to about 10 moles of ethylene oxide, and mixtures thereof and nonionic surfactants that are the condensation products of alcohols having an alkyl group containing from about 9 to about 15 carbon atoms with from about 4 to about 12 moles of ethylene oxide per mole of alcohol.

Particularly preferred anionic surfactants are the $C_{11-13}$ alkylbenzene sulfonates. Most preferred are the calcium salts of the $C_{11-13}$ alkylbenzene sulfonates.

Preparation of the Composition of the Present Invention

The following non-limiting examples represent methods of preparing the composition of the present invention.

EXAMPLE 1

A composition according to the present invention is prepared by blending Blend (a), Blend (b), and Component (c):

50% of Blend (a) containing 34% TETRONIC® 704 (element (i)), 46% calcium dodecylbenzene sulfonate (element (ii)) and 20% butanol (element (iii));

25% of Blend (b) containing 11% TETRONIC® 908 (element (i)), 69% calcium dodeylbenzene sulfonate (element (ii)) and 20% butanol (element (iii)); and 25% of Tergitol® XD (Component (c)).

EXAMPLE 2

A composition according to the present invention is prepared by blending Blend (a), Blend (b), and Component (c):

50% of Blend (a) containing 30% PLURONIC® P104 (element (i)), 50% calcium dodecylbenzene sulfonate (element (ii)) and 20% butanol (element (iii));

25% of Blend (b) containing 18% PLURONIC® F108 (element (i)), 62% calcium dodecylbenzene sulfonate (element (ii)) and 20% butanol (element (iii)); and 25% of Tergitol® XD (Component (c)).

EXAMPLE 3

A composition according to the present invention is prepared by blending Blend (a), Blend (b), and Component (c):

50% of Blend (a) containing 34% TETRONIC® 704 (element (i)), 46% calcium dodecylbenzene sulfonate (element (ii)) and 20% butanol (element (iii));

25% of Blend (b) containing 18% PLURONIC® F108 (element (i)), 62% calcium dodecylbenzene sulfonate (element (ii)) and 20% butanol (element (iii)); and 25% of Tergitol® XD (Component (c)).

The Utility of the Emulsifier Compositions of the Present Invention

The emulsifier compositions of the present invention are useful in preparing pesticidal formulations. The term pesticide is understood to encompass herbicides, insecticides, acaricides, nematicides, ectoparasiticides and fungicides. Examples of compound classes to which the pesticide in the emulsion may belong include ureas, triazines, triazoles, carbamates, phosphoric acid esters, dinitroanilines, morpholines, acylalanines, pyrethroids, benzilic acid esters, diphenylethers and polycyclic halogenated hydrocarbons. Pesticides which can be formulated with the emulsifier compositions of the present invention include, but are not limited to:

Ureas

Triasulfuron, Chlorobromuron, Chloroxuron, Chlorotoluron, Fluometuron, Thiazafluron.

Haloacetanilides

Metolachlor (2-chloro-6'-ethyl-N-(2-methoxy-1-methylethyl)acet-o-toluidide). Pretilachlor, Dimethachlor, Alachlor, Propachlor, Trimexachlor, acetochlor.

s-Triazines

Atrazin, Propazin, Terbutylazin, Ametryn, Aziprotryn, Cyromazin.

Triazole Derivatives

Propiconazole ((±)-1[2,4dichlorophenyl)-4-propyl-1.3-dioxolan-2-ylmethyl]-[H-1.2.4-triazole). Etaconazole. 1-[2-(2,4-dichlorophenyl)-pent-l-yl]-1H-1,2,4-triazole. Triadimefon. Difenoconazole. Penconazole (1-2,4-dichloroθ-propylphenethy)-1H-1,2,4-triazole).

Carbamates

Dioxacarb, Ethiofencarb, Furathiocarb, Aldicarb, Benomyl, 2-sec-butylphenylmethylcarbamate.

Phosphoric Acid Ester

Diazinon (O,O-diethyl O-2-isopropyl-6-methylpyrimidin-4-yl phosphorothioate). Methidathion. Isazofos (O-5-chloro-1-isopropyl-1H-1,2,4-triazol-3-yl O.O-diethyl phosphorothioate). Piperophos. Anilofos. Azinphos methyl. Isofenphos. Parathion. Malathion. Demeton. Fenamiphos. Fenthion. Fenitrothion. Fenchlorphos. Chlorfenvinphos. (2-chloro-1-(2,4-dichloro-phenyl)vinyl diethyl phosphate). Profenofos (O-4-bromo-2-chlorophenyl O-ethyl S-propyl phosphorothioate). Azamethiphos. Methacrifos.

Dinitroanilines

Pendimethalin, Isopropalin, Butralin, Fluchloralin, Profluralin.

Acylalanines

Metalaxyl, Fluralaxyl, Benzoylprop ethyl, Flamprop methyl.

Pyrethroids

Permethrin, Cypermethrin ((RS-I—cyano-3-phenoxybenzyl(IRS)-cis-trans-3-(2,2-dichlorovinyl) 1,1-dimethyl-cyclopropanecarboxylate), Fluvalinate, Resmethrin Fenvalerate, Fluvalinate, Tetramethrin, Cyhalotrin.

Benzilic Acid Esters

Bromoproylate, Chlorbenzylate, Chlorpropylate.

Diphenylether

Cis-trans-(±)-2-ethyl-5-(4-phenoxy-phenoxymethyl)-1,3-dioxolane.

Oximine

Pyrifenox (2',4'-dichloro-2-(3-pyridyl)acetophenone O-methyloxime).

Miscellaneous

Methopren, Flupropimorph, Tridemorph, Bromoxynil, Oxadiazon, Bupyrimate, Dicofol, Fenpropidin ((RS)-1-[3-(4-tert-butylphenyl)-2-methylpropyl]piperidine), Fenpropimorph, Fenoxycarb.

Preparation of Pesticidal Formulations Using the Emulsifier Composition of the Present Invention Pesticidal formulations are prepared, using the Applicants' emulsifier composition, by blending the selected pesticide, the Applicants' emulsifier composition and a hydrocarbon solvent (e.g. AROMATIC® 100 or 200 available from Exxon Chemical), such as ketones (e.g. cyclohexanone), methyl esters such as methyl laurate, and acetate esters such as the acetate ester of $C_9$–$C_{11}$ alcohols (EXXATE® 1000) and the acetate ester of a $C_6$ alcohol (EXXATE® 600, available from Exxon Chemical).

A pesticidal formulation can be prepared using the composition of the present invention according to the following non-limiting example: A blend which contains 60 parts acetochlor, 32 parts Exxate® 1000 and 8 parts of the composition of Example 1, hereinabove, is agitated on a vibrating mixer for one minute. The resulting blend is tested by diluting 5:95 parts with water. The dilution is measured for separation after 24 hours. No separation is observed.

What is claimed is:

1. An emulsifier composition comprising:
   (a) 1–90% of a blend consisting essentially of:
      (i) a polyoxyethylene (EO)/polyoxypropylene (PO) block copolymers selected from the group of compounds represented by Formula I, II or III or mixtures thereof:

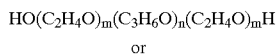

or

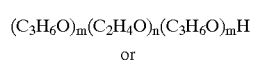

or

wherein Formula I, II and III all contain 10–40% EO, n has a value such that the molecular weight of the PO is about 1200–4000 for Formula I, 1500–4000 for Formula II and 500–6000 for Formula III;
      (ii) anionic surfactants;
      (iii) a solvent; and
   (b) 1–90% of a blend consisting essentially of:
      (i) a polyoxyethylene (EO)/polyoxypropylene (PO) block copolymer selected from the group of compounds represented by Formula I, II or III or mixtures thereof:

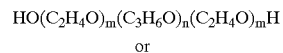

or

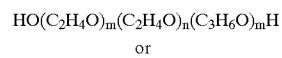

or

wherein Formula I, II and III all contain 50–80% EO, n has a value such that the molecular weight of the PO is about 1200–4000 for Formula I, 1500–4000 for Formula II and 500–6000 for Formula III;
      (ii) anionic surfactants;
      (iii) a solvent; and
   (c) 10–50% butyl ether of an EO/PO block copolymer.

2. An emulsifier composition according to claim 1 wherein the content of element (i) in blend (a) is 10–20% by weight.

3. An emulsifier composition according to claim 1 wherein element (a) (i) is Formula III.

4. An emulsifier composition according to claim 3 wherein element (b) (i) is Formula III.

5. An emulsifier composition according to claim 3 wherein the molecular weight of the PO hydrophobe is 3000–4000.

6. An emulsifier composition according to claim 1 wherein element (a) (i) is Formula I.

7. An emulsifier composition according to claim 6 wherein element (b) (i) is Formula I.

8. An emulsifier composition according to claim 6 wherein the PO is a hydrophobe, and the molecular weight of the PO hydrophobe is 3000–4000.

9. An emulsifier composition according to claim 3 wherein element (b) (i) is Formula I.

10. An emulsifier composition according to claim 9 wherein the molecular weight of the PO hydrophobe for is 3000–4000.

11. An emulsifier composition according to claim 1 wherein said solvent (iii) in blend (a) and blend (b) is n-butanol.

* * * * *